United States Patent [19]

Okamoto et al.

[11] 4,441,981
[45] Apr. 10, 1984

[54] GAS SENSOR

[75] Inventors: Hiroshi Okamoto, Ohme; Michiharu Seki, Kodaira; Hidehito Ohayashi, Tokyo, all of Japan

[73] Assignee: Hitachi, Ltd., Tokyo, Japan

[21] Appl. No.: 169,137

[22] Filed: Jul. 15, 1980

Related U.S. Application Data

[63] Continuation of Ser. No. 36,862, May 7, 1979, abandoned.

[30] Foreign Application Priority Data

May 10, 1978 [JP] Japan .................................. 53-54501

[51] Int. Cl.³ ............................................. G01N 27/58
[52] U.S. Cl. .................................................... 204/426
[58] Field of Search .............. 204/195 S, 1 S; 60/276; 123/489; 422/98

[56] References Cited

U.S. PATENT DOCUMENTS

| | | | |
|---|---|---|---|
| 3,935,089 | 1/1976 | Togawa et al. | 204/195 S |
| 3,962,866 | 6/1976 | Neidhard et al. | 60/276 |
| 3,974,054 | 8/1976 | Poolman et al. | 204/195 S |
| 4,005,001 | 1/1977 | Pebler | 204/195 S |
| 4,132,615 | 1/1979 | Linder et al. | 204/195 S |
| 4,157,282 | 6/1979 | Riddel | 204/1 T |

FOREIGN PATENT DOCUMENTS

| | | | |
|---|---|---|---|
| 52-14639 | 4/1977 | Japan . | |
| 2004067 | 3/1979 | United Kingdom | 422/98 |

*Primary Examiner*—G. L. Kaplan
*Attorney, Agent, or Firm*—Antonelli, Terry & Wands

[57] ABSTRACT

A gas sensor wherein a first electrode whose surface is covered with an oxidizing catalyst, and a second electrode which is made of the same material as that of the first electrode and whose surface is exposed and can come into direct contact with a gas to-be-detected are disposed on a solid electrolyte which exhibits an oxygen ion conductivity.

Since the gas sensor of this invention has the electrodes formed of the identical material, it has over a prior-art gas sensor the merits that secular changes are very little and that the operation is possible even at low temperatures. It can readily detect a combustible gas on the order of several tens p.p.m.

19 Claims, 8 Drawing Figures

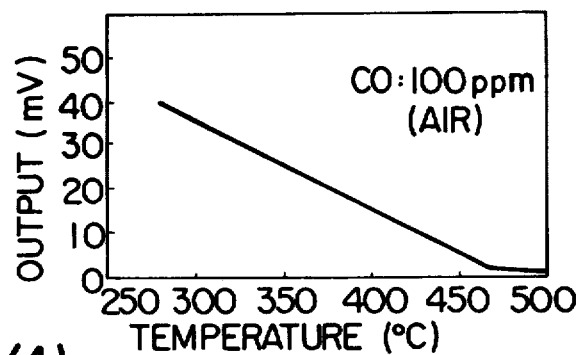
FIG. 4
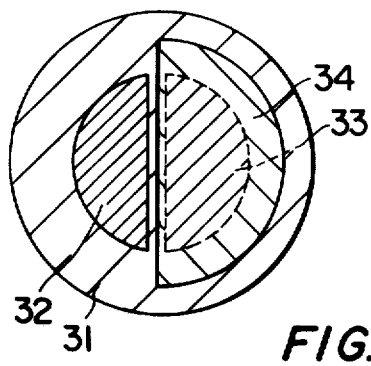
FIG. 5(A)
FIG. 5(B)
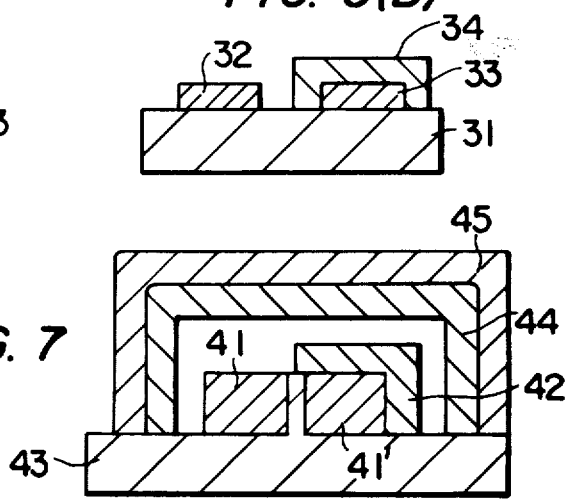
FIG. 7
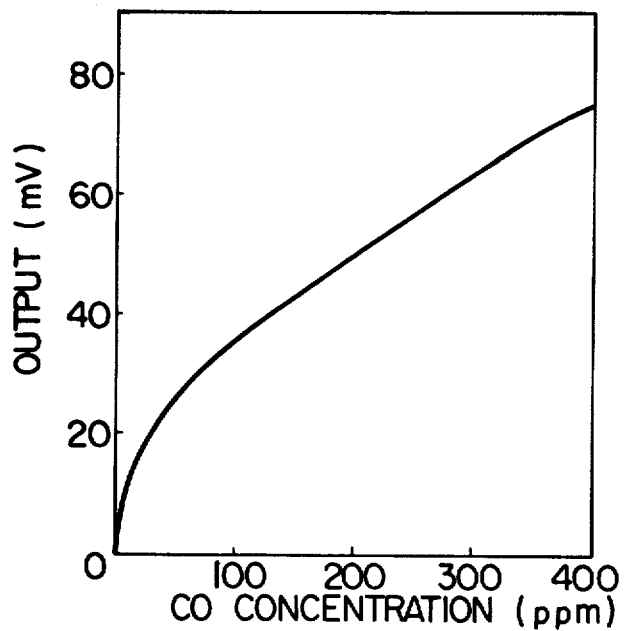
FIG. 6

GAS SENSOR

This is a continuation of Ser. No. 36,862 filed May 7, 1979 and now abandoned.

BACKGROUND OF THE INVENTION

1. Field of the Invention

This invention relates to a gas sensor. More particularly it relates to a gas sensor capable of sensing and detecting various combustible gases such as carbon monoxide, propane gas, town gas and hydrogen.

2. Description of the Prior Art

When the various combustible gases exist in an atmosphere, there are toxicity to organisms and danger of explosion. Therefore, various gas sensors capable of detecting the gases have been proposed.

The known gas sensors exploit resistance variations, oxidizing reaction heat, electrochemical reactions, etc.

A typical gas sensor utilizing electrochemical reactions among the prior-art gas sensors is disclosed in U.S. Pat. No. 4,005,001 and Japanese Patent Application Publication No. 14639/1977.

This gas sensor is such that electrodes made of materials whose catalytic activities to oxygen and combustible gases are different from each other are disposed on the surfaces of a solid electrolyte which has an oxygen ion-conductivity. When the gas sensor having such a structure is placed in a gas containing both the combustion gas and oxygen, an electromotive force corresponding to the concentration of the combustible gas is generated across both the electrodes because the electrodes have the different catalytic activities as described above.

This sensor, however, has the disadvantage that since the materials of the electrodes deposited on both the surfaces of the solid electrolyte are different, the electrodes exhibit different secular changes, so the characteristics of the sensor undergo conspicuous secular changes.

The detection sensitivity is approximately 1% in case of, for example, CO, and it is difficult and very unsatisfactory in practical use to detect a smaller quantity of CO. Moreover, the operating temperature is as high as about 650° C., which leads to problems on the lifetime, the power dissipation etc.

SUMMARY OF THE INVENTION

An object of this invention is to solve the problems of the prior-art gas sensor and to provide a combustible gas sensor which exhibits little secular changes, which has a low operating temperature and which has a sufficiently high detection sensitivity.

In order to accomplish the object, according to this invention, electrodes made of an identical substance are respectively deposited on a solid electrolyte, and one of the electrodes is covered with a catalyst capable of oxidizing combustible gases.

BRIEF DESCRIPTION OF THE DRAWINGS

FIGS. 3 and 4 are graphs respectively showing the influences of the concentration and the operating temperature in an embodiment of this invention, FIGS. 5(A) and 5(B) and FIG. 6 are diagrams respectively showing the structure and sensitivity of another embodiment of this invention, and FIG. 7 is a model view showing another embodiment of this invention.

DETAILED DESCRIPTION

Figure 1:
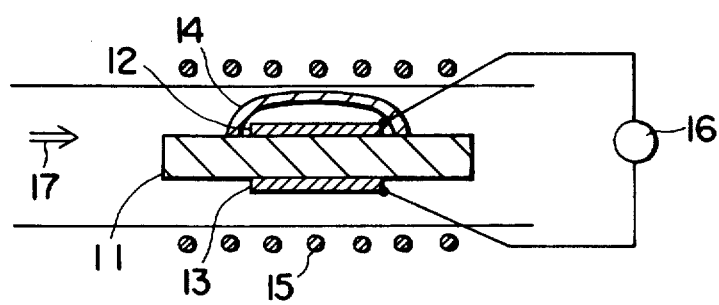
FIG. 1 is a model view for illustrating the construction of this invention.

FIG. 1 is a model view for explaining the construction of an embodiment of this invention.

A solid electrolyte 11 having an oxygen ion-conductivity is made of $ZrO_2$-$Y_2O_3$. Electrodes 12 and 13 made of platinum are deposited on both the surfaces of the solid electrolyte. As seen from FIG. 1, the second electrode 13 has its surface exposed and therefore comes into direct contact with a gas to-be-detected 17. In contrast, the first electrode 12 is covered with an alumina supported platinum catalyst 14 which is a catalyst adapted to oxidize combustible gases. The sensor is held at 200°–700° C. by a heater 15. Air containing the combustible gas flows in the direction of arrow 17, and an electromotive force generated between both the electrodes 12 and 13 is indicated on an indicating instrument 16.

Briefly stated, the operating principle of the gas sensor having the above structure is as follows.

When air containing a very small quantity of combustible gas is brought into contact with the gas sensor, the second electrode 13 comes into direct contact with the air 17 containing the combustible gas. Since, however, the first electrode 12 is covered with the oxidizing catalyst 14, the combustible gas contained in the air is oxidized by the oxidizing catalyst 14 and does not reach the electrode 12. As a result, an electromotive force is generated across both the electrodes 12 and 13.

Figure 2:
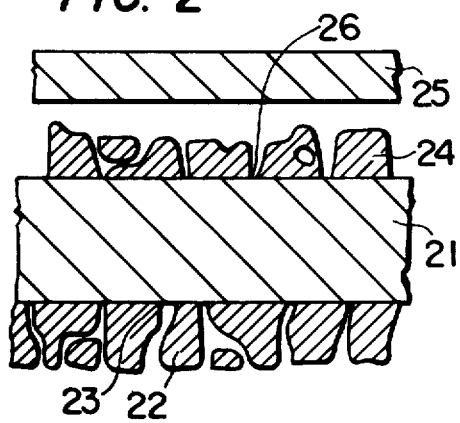
FIG. 2 is a model view for explaining the operating principle of this invention.

More in detail, unless the oxidizing catalyst exists, the combustible gas such as CO is uniquely adsorbed onto the interface 23 of three phases consisting of the solid electrolyte 21, the second electrode 22 and the gas shown in FIG. 2. Therefore, oxygen contained in the air is hindered from being adsorbed onto the three-phase interface 23, and the partial pressure of oxygen at the three-phase interface becomes much lower than the partial pressure of oxygen in the air.

On the other hand, regarding the first electrode 24 covered with the porous oxidizing catalyst 25, the very small quantity of combustible gas contained in the air does not get to the first electrode 24 because it is oxidized by the oxidizing catalyst 25. Therefore, the partial pressure of oxygen at the interface 26 of three phases is almost equal to the partial pressure of oxygen of the air.

In this way, a marked difference develops between the oxygen concentrations at the three-phase interfaces of the second electrode 22 and the first electrode 24. Therefore, an oxygen concentration cell is formed, and the electromotive force is generated. Since this electromotive force corresponds to the combustible gas concentration in the air, the concentration of the combustible gas can be evaluated by measuring the electromotive force.

The sensor according to this invention has the electrodes of the identical material respectively deposited on the solid electrolyte as described above. Accordingly, even when the electrodes undergo secular changes, the changes of both the electrodes take place in the same manner, and the sensor has the lifetime noticeably improved as compared with the prior-art sensor.

As will be described later, also the operating temperature can be lowered down to about 300° C. which is much lower than about 650° C. in the prior art. Needless to say, the power dissipation is low. The lifetime characteristic is also improved from this aspect.

EXAMPLE 1

As a solid electrolyte conducting oxygen ions, there was employed stabilized zirconia in which the molar ratio of $ZrO_2:Y_2O_3$ was 92:8. It was molded and baked to fabricate a disc which had a thickness of 1–2 mm and a diameter of about 20 mm.

Platinum films each being 0.22 μm thick were deposited on both the surfaces of the disc as electrodes by the electron-beam evaporation.

The surface of one of the electrodes was covered with about 50 mg of a platinum catalyst. (This platinum catalyst was prepared by immersing $v\text{-}Al_2O_3$ in a solution of chloroplatinic acid and reducing it after drying. The quantity of platinum was approximately 5%.)

While a sensor thus fabricated was held at approximately 300° C., the CO concentration in air and the electromotive force between both the electrodes were measured. Then, a result shown in FIG. 3 was obtained.

Figure 3:
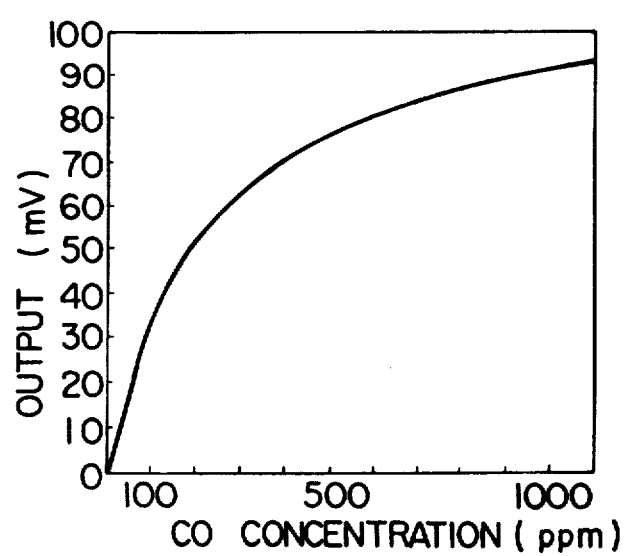

As apparent from FIG. 3, the sensor according to this invention can satisfactorily detect CO on the order of several tens p.p.m. existent in the air or the like.

FIG. 4 shows the relationship between the operating temperature and the generated electromotive force as obtained under the condition under which the sensor according to this invention was put in air containing 100 p.p.m. of CO. As seen from the figure, the sensor of this invention can be used at temperatures which are much lower than the operating temperature of the prior-art sensor, and an extraordinarily high electromotive force is obtained at a temperature of 300° C. or so.

At temperatures below 250° C., the resistance of the gas sensor itself becomes conspicuously high. In practical use, therefore, the sensor is preferably used at temperatures of and above 250° C. The upper limit of the operating temperature at which the sensor could be used was about 450° C. as apparent from FIG. 4.

EXAMPLE 2

Electrodes were formed in such a way that a liquid in which a fine powder of platinum was dispersed was applied on both the surfaces of the disc of the stabilized zirconia referred to in Example 1, whereupon it was dried at 500° C. One of the electrodes was covered with the platinum alumina catalyst by the same method as in Example 1.

The characteristics of a sensor thus fabricated were nearly the same as in case of Example 1.

Even when other Pt-group elements or gold was employed instead of platinum as the electrode material, substantially the same results were obtained.

As the oxygen ion-conducting solid electrolyte in this invention, a large number of materials such as $ZrO_2\text{-}CaO$, $CeO_2\text{-}Gd_2O_3$, $Y_2O_3\text{-}CeO_2$, $Nb_2O_5\text{-}Bi_2O_3$ and $Y_2O_3\text{-}Bi_2O_3$ can be used besides the aforecited material $ZrO_2\text{-}Y_2O_3$.

As the oxidizing catalyst, oxides of V, Cr, Cu, Mo, W, Fe, Ni, Co and Mn, and platinum group elements such as Pt, Ru, Rh and Pd can be used singly or in combination. As the catalyst support, ones usually employed such as alumina, silica and titanium oxide can be similarly used. The range of the relative weight percent of the catalytic component is about 0.1~20 weight percent with respect to the catalytic support.

EXAMPLE 3

In both the above examples, the electrodes were deposited on both the surfaces of the oxygen ion-conducting solid electrolyte disc. In this invention, however, two electrodes may be deposited on an identical surface of a solid electrolyte disc.

Structures in plan and in section in this example are respectively shown in FIGS. 5(A) and 5(B) in a model-like fashion. On a $ZrO_2:Y_2O_3$ (having a molar ratio of 92:8) disc 31 which was 1–2 mm in thickness and 20 mm in diameter, electrodes were formed by depositing semicircular platinum films 32 and 33 with a diameter of 12 mm and a thickness of 0.22 μm by the electron-beam evaporation. The surface of the first electrode 33 was covered with the same porous platinum catalyst 34 as described in Example 1. Thus, a sensor was fabricated.

When holding the sensor at 300° C., the relationship between the CO concentration in air and the electromotive force was evaluated. Then, about 30 ppm of CO could be satisfactorily detected as illustrated in FIG. 6.

Although both the electrodes 32 and 33 were made semicircular in this example, they may of course be put into other shapes. Favorable results were obtained also in case where one of the electrodes was made circular and the other was made annular and where the electrodes were concentrically arranged.

EXAMPLE 4

As shown in FIG. 7, platinum electrodes 41 and 41' were formed on a substrate 43 which was made of an oxygen ion-conducting solid electrolyte of stabilized zirconia containing 8 mol-% of $Y_2O_3$. One electrode 41' was covered with a porous oxidizing catalyst layer 42 which was made of platinum alumina. Further, the electrodes were covered with an electrically insulating porous layer 44 made of MgO and an active carbon layer 45. Thus, a sensor was formed.

Powers required for holding sensors at 300° C. were compared. When the electrically insulating layer 44 was disposed, the required power decreased about 40%. When both the electrically insulating layer 44 and the active carbon layer 45 were disposed, the required power decreased 10% more. It was accordingly noted that the layers are very effective for the reduction of power dissipation.

Active carbon adsorbs $SO_2$, hydrocarbon gases etc. well, and scarcely adsorbs CO, $H_2$, $CH_4$ etc. Therefore, it can prevent the sensor from being tainted by dust, mist and the gases, and it can prevent the characteristics of sensors for CO etc. from lowering for a long term.

What is claimed is:

1. A gas sensor comprising a solid electrolyte which has an oxygen ion conductivity, a first electrode which is covered with an oxidizing catalyst for oxidizing a combustible gas to-be-detected contained in air, and a second electrode which is made of the same material as that of said first electrode and having a surface that comes into direct contact with the air containing the gas to-be-detected, said oxidizing catalyst and said first and second electrodes being disposed on said solid electrolye, and means for causing the air containing the gas to-be-detected to contact the oxidizing catalyst covering the first electrode and the contact surface of the second electrode so that the concentration of the combustible gas contained in the air is sensed and known from an electromotive force generated across said first and second electrodes.

2. A gas sensor according to claim 1, wherein said first and second electrodes are respectively arranged on different surfaces of said solid electrolyte.

3. A gas sensor according to claim 1, wherein said first and second electrodes are arranged on an identical surface of said solid electrolyte.

4. A gas sensor according to claim 1, wherein said solid electrolyte is a member selected from the group consisting of $ZrO_2\text{-}Y_2O_3$, $ZrO_2\text{-}CaO$, $CeO\text{-}Gd_2O_3$, $Y_2O_3\text{-}CeO_2$, $Nb_2O_5\text{-}Bi_2O_3$ and $Y_2O_3\text{-}Bi_2O_3$.

5. A gas sensor according to claim 4, wherein the material of said electrodes is a member selected from the group consisting of Pt-group elements and Au.

6. A gas sensor according to claim 5, wherein said oxidizing catalyst is at least one member selected from the group consisting of oxides of V, Cr, Cu, Mo, W, Fe, Ni, Co and Mn, and the elements Pt, Ru, Rh and Pd.

7. A gas sensor according to claim 1, wherein said sensor includes means for indicating the electromotive force generated across said first and second electrodes.

8. A gas sensor according to claim 1, wherein said oxidizing catalyst is a porous material.

9. A gas sensor comprising a solid electrolyte which has an oxygen ion conductivity, a first electrode which is covered with an oxidizing catalyst for oxidizing a combustible gas to-be-detected in a gas mixture, and a second electrode which is made of the same material as that of the first electrode and having a surface that comes into direct contact with the gas mixture containing the gas to-be-detected, said first and second electrodes being disposed and arranged on an identical surface of said solid electrolyte, and means for causing the gas mixture containing the gas to-be-detected to contact the oxidizing catalyst covering the first electrode and the contact surface of the second electrode so that the concentration of the combustible gas contained in the gas mixture is sensed and known from an electromotive force generated across said first and second electrodes, said gas sensor further comprising an electrically insulating layer means covering the first and second electrodes whereby there is a reduction of power dissipation from said electrodes.

10. A gas sensor according to claim 9, wherein said electrically insulating layer means is covered with a layer of active carbon.

11. A gas sensor according to claim 1, further comprising means for maintaining the solid electrolyte, the first electrode, the second electrode and the oxidizing catalyst at a temperature ranging from 250°–450° C.

12. A gas sensor according to claim 1, wherein the means for causing the gas to be detected to contact the oxidizing catalyst covering the first electrode and the contact surface of the second electrode comprises means for directing air containing the combustible gas to be detected over the oxidizing catalyst and the contact surface of the second electrode.

13. A gas sensor according to claim 11, wherein said gas sensor further comprises means for heating the air containing the combustible gas to be detected, the solid electrolyte, the first electrode, the second electrode, and the oxidizing catalyst to a temperature in the range of from 250°–450° C.

14. A gas sensor according to claim 1, wherein said gas sensor further comprises heating means arranged for heating said gas mixture, said oxidizing catalyst and said contact surface of the second electrode, said heating means being arranged in the proximity of said oxidizing catalyst and said contact surface.

15. A gas sensor according to claim 1, wherein said first and second electrodes are capable of determining the presence of a combustible gas in a concentration of 30 to 1000 ppm in the air.

16. A gas sensor for detecting a very small concentration of a combustible gas in air comprising a solid electrolyte which has an oxygen ion conductivity, a first electrode which is covered with a porous oxidizing catalyst for oxidizing a combustible gas to-be-detected contained in the air and for preventing the combustible gas from contacting the first electrode while allowing air to contact the first electrode, and a second electrode which is made of the same material as that of the first electrode and having a surface that comes into direct contact with the air containing the combustible gas to-be-detected, said oxidizing catalyst and said first and second electrodes being disposed on said solid electrolyte, and means for causing the air containing the combustible gas to-be-detected to contact the oxidizing catalyst covering the first electrode and to contact the contact surface of the second electrode so that the concentration of the combustible gas contained in the air is sensed and known from an electromotive force which is generated across said first and second electrodes and which is dependent on the concentration of the combustible gas in the air contacted with the contact surface of the second electrode.

17. A gas sensor according to claim 16, further comprising means for heating the solid electrolyte, the first electrode, the second electrode and the oxidizing catalyst at a temperature ranging from 250°–450° C.

18. A gas sensor according to claim 17, wherein said heating means is arranged in the immediate proximity of said oxidizing catalyst and said contact surface of the second electrode.

19. A gas sensor according to claim 18, wherein said first and second electrodes are capable of detecting the presence of a combustible gas in air having a concentration in the range of from 30–1000 ppm.

* * * * *